(12) United States Patent
Niwa

(10) Patent No.: US 10,874,785 B2
(45) Date of Patent: Dec. 29, 2020

(54) COMPONENT CONCENTRATION SENSING SYSTEM

(71) Applicant: TORAY ENGINEERING CO., LTD., Tokyo (JP)

(72) Inventor: Tsukasa Niwa, Otsu (JP)

(73) Assignee: TORAY ENGINEERING CO., LTD., Tokyo (JP)

( * ) Notice: Subject to any disclaimer, the term of this patent is extended or adjusted under 35 U.S.C. 154(b) by 18 days.

(21) Appl. No.: 16/476,186

(22) PCT Filed: Dec. 8, 2017

(86) PCT No.: PCT/JP2017/044119
§ 371 (c)(1),
(2) Date: Jul. 5, 2019

(87) PCT Pub. No.: WO2018/131348
PCT Pub. Date: Jul. 19, 2018

(65) Prior Publication Data
US 2020/0023114 A1    Jan. 23, 2020

(30) Foreign Application Priority Data
Jan. 11, 2017   (JP) ................. 2017-002744

(51) Int. Cl.
*G01N 21/05* (2006.01)
*A61M 1/16* (2006.01)
(Continued)

(52) U.S. Cl.
CPC ............... *A61M 1/16* (2013.01); *G01N 21/05* (2013.01); *G01N 21/33* (2013.01); *G01N 21/59* (2013.01)

(58) Field of Classification Search
CPC .... A61M 1/3693; A61M 1/16; A61M 1/1605; A61M 1/1609; A61M 2205/3313;
(Continued)

(56) References Cited

U.S. PATENT DOCUMENTS

| 6,284,142 B1 * | 9/2001 | Muller | ............... A61M 1/30 210/745 |
| 7,422,693 B2 * | 9/2008 | Carter | ............... B04B 13/00 210/512.1 |

(Continued)

FOREIGN PATENT DOCUMENTS

JP    2009-222412 A    10/2009

OTHER PUBLICATIONS

International Search Report of the corresponding International Application No. PCT/JP2017/044119, dated Feb. 27, 2018.

*Primary Examiner* — Irakli Kiknadze
(74) *Attorney, Agent, or Firm* — Global IP Counselors, LLP

(57) ABSTRACT

A component concentration sensing system includes a first component concentration sensor, a collector and a second component concentration sensor. The first component concentration sensor is provided to a channel through which flows a liquid whose component concentration is to be sensed, and is configured to irradiate the liquid with light and sense the component concentration in the liquid from a degree of light absorption. The collector is arranged to collect the liquid flowing through the channel. The second component concentration sensor is configured to irradiate the liquid collected in the collector with light and sense the component concentration in the liquid from the degree of light absorption.

8 Claims, 8 Drawing Sheets

(51) Int. Cl.
*G01N 21/33* (2006.01)
*G01N 21/59* (2006.01)

(58) Field of Classification Search
CPC .. A61M 2205/3331; A61M 2205/3393; A61M 2205/50; A61M 5/1486; A61M 1/1692; A61M 1/367; A61M 2205/3306; A61M 1/1619; A61M 1/3609; A61M 2202/0498; A61M 2205/15; B04B 13/00; B04B 2013/006; G01N 15/042; G01N 15/05; G01N 2015/047; G01N 21/05; G01N 21/33; G01N 21/59; G01N 21/85; G01N 21/274; G01N 2201/062; G01N 2201/0621; A61B 2560/0406; A61B 2562/182; A61B 5/0071; A61B 5/14546; A61B 5/1455; A61B 5/6887; G02B 2027/0127; G02B 2027/0138; G02B 2027/014; G02B 2027/0178; G02B 2027/018

USPC .............. 250/373; 210/94, 96.2, 321.6, 646; 356/39, 448

See application file for complete search history.

(56) References Cited

U.S. PATENT DOCUMENTS

| | | | |
|---|---|---|---|
| 8,518,247 B2* | 8/2013 | Akita | G01N 21/274 210/94 |
| 9,801,993 B2* | 10/2017 | Barrett | F16B 2/22 |
| 10,281,454 B2* | 5/2019 | Barrett | A61M 1/14 |
| 10,426,387 B2* | 10/2019 | Barrett | G01J 1/0214 |

* cited by examiner ized. The functional state of# COMPONENT CONCENTRATION SENSING SYSTEM

CROSS-REFERENCE TO RELATED APPLICATIONS

This application is a U.S. National stage of International Application No. PCT/JP2017/044119 filed on Dec. 8, 2017. This application claims priority to Japanese Patent Application No. 2017-002744 filed on Jan. 11, 2017 with Japan Patent Office. The entire disclosure of Japanese Patent Application No. 2017-002744 is hereby incorporated herein by reference.

BACKGROUND

Field of the Invention

The present invention relates to a system for irradiating a liquid with light and measuring the component concentration in the liquid from the degree of light absorption, and more particularly relates to a component concentration sensing system capable of measuring an albumin concentration.

Background Information

Patients with renal failure are treated with hemodialysis therapy using a hemodialysis device that artificially substitutes for kidney function (see Japanese Patent Application Publication No. 2009-222412 (Patent Literature 1), for example). In this hemodialysis device, as shown in FIG. 8, a dialyzer 100 (a blood purification device) is provided along the blood circulation path, and a dialysate circuit that supplies dialysate to this dialyzer 100 is provided. Extracorporeal circulation is then performed in which blood collected from the patient is sent back into the body via the dialyzer 100, and while this extracorporeal circulation is being performed, waste products and excess water in the blood are removed as effluent by the dialysate that is supplied to the dialyzer 100 through the semipermeable membrane of the dialyzer 100.

Also, the hemodialysis device is provided with a component concentration sensing system 101, and the condition of a patient under dialysis can be ascertained by measuring a specific component concentration in the effluent from the dialyzer 100. That is, the dialysis state of a patient under dialysis can be ascertained in real time by measuring the concentrations of urea, uric acid, and other such waste materials in the circulating effluent.

As shown in FIG. 8, the component concentration sensing system 101 is formed by a component concentration sensor 102 that is connected to the effluent channel from the dialyzer 100, and a monitoring device 103 (analyzer) that is connected to the component concentration sensor 102. This component concentration sensor 102 is formed such that a change in concentration can be measured by sensing the degree of light absorption of the effluent from the dialyzer 100. That is, a liquid cell portion that circulates the effluent (also referred to simply as a liquid) is irradiated with light (UV light, for example), and the light after absorption by the liquid flowing through the liquid cell portion is detected by a light receiver, allowing the concentration of the liquid to be sensed. The sensing result from the component concentration sensor 102 is monitored by the monitoring device 103 so that the dialysis state can be ascertained in real time.

SUMMARY

The effluent here contains albumin, which is an indicator of the patient's nutritional state, and the functional state of the liver and kidneys, as well as the nutritional state, etc. (referred to as the health state), can be ascertained by monitoring this albumin concentration. Usually, the measurement of albumin concentration involves the use of dye binding, which is a method that makes use of changes in coloring attributable to the binding of albumin to a specific dye. That is, after extracting some of the effluent and allowing the albumin to absorb a specific dye, the albumin concentration is measured by quantifying from the absorption wavelength of the dye (BCG method, BCP method, etc.). Therefore, sensing in real time by the component concentration sensor 102 is difficult, and another problem is that it is extremely difficult to ascertain the dialysis state and the health state with the shared component concentration sensing system 101.

The present invention was conceived in light of the above problems, and it is an object thereof to provide a component concentration sensing system capable of sensing the component concentration of a liquid that is delivered, while simultaneously sensing the albumin concentration with a shared liquid delivery circuit.

In order to solve the above problems, the component concentration sensing system of the present invention comprises a first component concentration sensor that is provided to a channel through which flows a liquid whose component concentration is to be sensed, and that irradiates the liquid with light and senses the component concentration in the liquid from the degree of light absorption; a collector that collects the liquid flowing through the channel; and a second component concentration sensor that irradiates the liquid collected in the collector with light and senses the component concentration in the liquid from the degree of light absorption.

With the above-mentioned component concentration sensing system, the second component concentration sensor can sense the albumin concentration. That is, the collector is provided within the liquid delivery circuit, and the second component concentration sensor is attached to the collector. The liquid collected in the collector (the effluent from the dialyzer) is irradiated with light (such as UV light) from the second component concentration sensor, whereby the albumin in the liquid is modified by the light, and this irradiating light can be received to sense the albumin concentration in the collector. Therefore, the concentration of urea, uric acid, etc., is measured by the first component concentration sensor to determine the dialysis state, and at the same time the albumin concentration is sensed by the second component concentration sensor in the shared liquid delivery circuit, thereby allowing the health state to be ascertained.

The configuration may be such that the collector is formed by a branched channel that branches off from the channel to which the liquid is fed, and a valve that is provided to the branched channel, and the second component concentration sensor senses the component concentration of the liquid collected in the branched channel.

With this configuration, the collector is formed in the branched channel by closing the valve of the branched channel, and the second component concentration sensor is provided to this collector, which means that the albumin concentration can be sensed, and because the first component concentration sensor is provided to a channel that is separate from the branched channel, the concentration of urea, uric acid, etc., and the concentration of albumin with can be sensed simultaneously with a simple configuration.

Also, the configuration may be such that the first and second component concentration sensors have an irradiation component that emits light, a light receiver that receives light emitted from the irradiation component, and a liquid cell portion that is disposed between the irradiation component and the light receiver and through which the liquid flows, and the liquid cell portion is formed of a cylindrical tube.

With this configuration, using a cylindrical tube for the liquid cell portion of the component concentration sensor allows the component concentration sensor to be configured at low cost, so the cost of the system as a whole can be reduced.

Also, as a specific mode of the above-mentioned component concentration sensing system, the liquid is an effluent discharged from a blood purification device, and the wavelength of the light that irradiates this effluent is 240 to 260 nm.

With the component concentration sensing system of the present invention, the component concentration of the liquid to be delivered can be sensed, while simultaneously sensing the concentration of albumin with a shared liquid delivery circuit.

DETAILED DESCRIPTION OF EMBODIMENTS

An embodiment of the component concentration sensing system of the present invention will be described with reference to the drawings.

Figure 1:
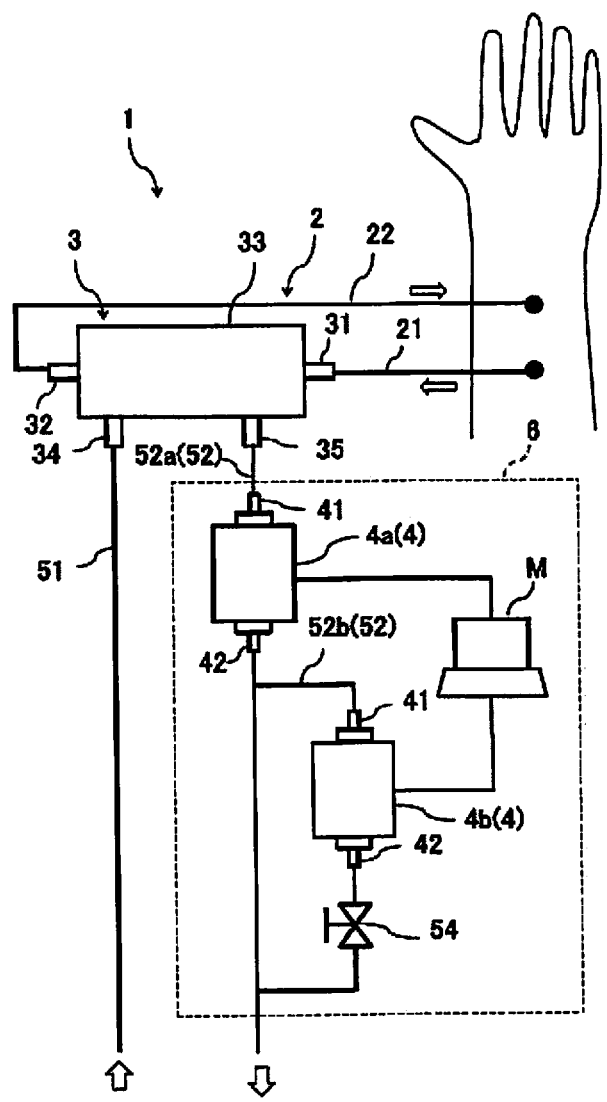
FIG. 1 is a path diagram showing a hemodialysis device to which the component concentration sensing system of the present invention is applied.

FIG. 1 is a path diagram showing a hemodialysis device that makes use of a component concentration sensor in an embodiment of the present invention.

As shown in FIG. 1, a hemodialysis device 1 has a blood circulation channel 2 that extracorporeally circulates the patient's blood, a dialyzer 3 that is provided along the blood circulation channel 2 and purifies the blood, an effluent line 52 (an effluent channel) for discharging the effluent (also called a liquid) from the dialyzer 3, and a supply line 51 (a supply channel) for supplying dialysate to the dialyzer 3.

The blood circulation channel 2 is formed by a flexible tube, and has an outgoing path portion 21 for circulating blood collected from the patient, and a return path portion 22 for returning the purified blood to the patient. The outgoing path portion 21 and the return path portion 22 connect the patient and the dialyzer 3, and when a pump (not shown) is driven, blood collected from the patient passes through the dialyzer 3 via the outgoing path portion 21, and the blood purified by the dialyzer 3 is returned to the patient via the return path portion 22.

The dialyzer 3 is used to purify the supplied blood and to eliminate water, and has an inlet port 31 and an outlet port 32. That is, the forward path portion 21 is connected to the inlet port 31, and the return path portion 22 is connected to the outlet port 32, so the patient's blood is supplied to the dialyzer 3 through the inlet port 31, and blood that has been purified by the dialyzer 3 is returned to the patient through the outlet port 32. This dialyzer 3 is designed so that a plurality of hollow fibers are held in a container body 33, and blood passes through these hollow fibers. Small through-holes are formed in the hollow fibers, and when blood passes through the hollow fibers, waste products and excess water are passed through the dialysate filling the container body 33 via these through-holes, and the blood is purified.

The supply line 51 and the effluent line 52 are formed by flexible tubes, and are each connected to the dialyzer 3. More specifically, the dialyzer 3 has a supply port 34 to which dialysate is supplied, and an effluent port 35 to discharge the dialysate, the supply line 51 is connected to the supply port 34, and the effluent line 52 is connected to the effluent port 35. Therefore, the dialysate is supplied from a dialysate supply source (not shown), through the supply line 51, to the dialyzer 3, a dialysis treatment is performed in the container body 33 of the dialyzer 3, and then the used dialysate is discharged as effluent (the liquid of the present invention) through the effluent line 52.

Also, a component concentration sensing system 6 is provided to the effluent line 52. This component concentration sensing system 6 is used to measure the component concentration of the effluent discharged from the dialyzer 3 and thereby ascertain the condition of the patient during dialysis. The component concentration sensing system 6 has a first component concentration sensor 4a that senses a specific concentration in the blood circulating extracorporeally, a collector that collects the liquid flowing in the effluent line, and a second component concentration sensor 4b that is provided to this collector.

The effluent line 52 has a main channel 52a that is connected directly to the effluent port 35, and a branched channel 52b that branches off from the main channel 52a. The first component concentration sensor 4a is provided to the main channel 52a, and the second component concentration sensor 4b is provided to the branched channel 52b. A valve 54 is provided to the branched channel 52b, and liquid in the branched channel 52b can be circulated by opening and closing this valve 54. That is, when the valve 54 is opened, the liquid flows from the main channel 52a into the branched channel 52b, and the liquid can be sent through the branched channel 52b. When the valve 54 is closed, the flow of the liquid through the branched channel 52b is stopped, and the liquid can be collected in the branched channel 52b. That is, closing the valve 54 forms a collector 56 (see FIG. 7) in the branched channel 52b. The second component concentration sensor 4b is provided upstream of this collector 56, that is, the valve 54.

In this embodiment, the first component concentration sensor 4a and the second component concentration sensor 4b are formed in the same configuration. Therefore, the first component concentration sensor 4a and the second component concentration sensor 4b shall be described together and shall be referred to simply as the component concentration sensors 4 unless it is necessary to refer to the first component concentration sensor 4a and the second component concentration sensor 4b separately.

The component concentration sensors 4 are used to sense the component concentration of the liquid flowing through the effluent line 52 in real time. Each component concentration sensor 4 irradiates the liquid flowing in the effluent line 52 with light, and senses the component concentration in the liquid from the degree of absorption of this light. The component concentration sensors 4 in this embodiment are each connected to a monitoring device M, and the monitoring device M monitors the sensing result sensed by the component concentration sensors 4, and adjusts the various settings of the component concentration sensors 4.

Figure 2A:
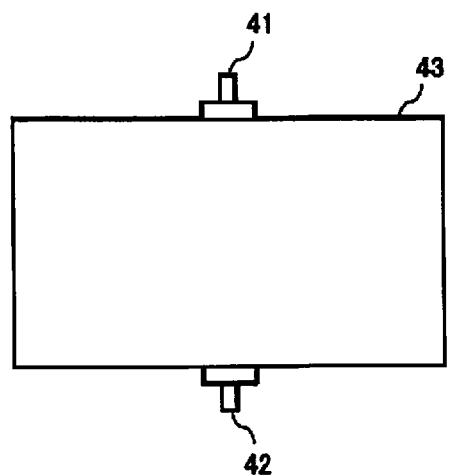
FIGS. 2A and 2B are diagrams of the component concentration sensor, with FIG. 2A being a diagram of the external appearance, and FIG. 2B a diagram of the interior.
Figure 2B:
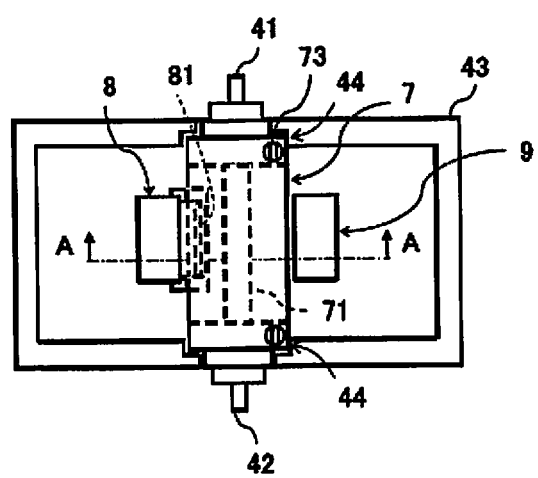

As shown in FIGS. 2A and 2B, the component concentration sensor 4 has a cell unit 7, a lamp unit 8, and an effluent monitor 9 in a housing 43 having an inlet 41 and an outlet 42. FIG. 2A shows the external appearance of the component concentration sensor 4, and FIG. 2B shows the state when the lid of the housing 43 has been removed. The housing 43 is a box-shaped case member, the cell unit 7 is accommodated in the center portion thereof, and the lamp unit 8 and the effluent monitor 9 are accommodated so as to sandwich the cell unit 7. That is, the liquid flowing to the cell unit 7 is irradiated with UV light from the lamp unit 8, and the UV light passing through the liquid is received by the effluent monitor 9, so that the component concentration in the liquid can be sensed.

The cell unit 7 circulates the liquid in the effluent line 52, and comprises the inlet 41 and the outlet 42 connected to the effluent line 52. That is, the inlet 41 is connected to the upstream side of the effluent line 52 and the outlet portion 42 is connected to the downstream side of the effluent line 52, so that the liquid discharged from the dialyzer 3 passes through the cell unit 7 via the inlet 41, and flows from the outlet 42 back to the effluent line 52. More specifically, the first component concentration sensor 4a is connected to the upstream side of the main channel 52a and the inlet portion 41, and is connected to the outlet portion 42 and the downstream side of the main channel 52a. The second component concentration sensor 4b is connected to the upstream side of the branch passage 52b and the inlet 41, and is connected to the downstream side of the branch passage 52b and the outlet 42.

Figure 3A:
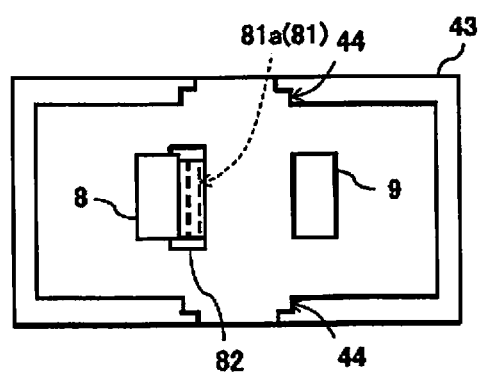
FIGS. 3A and 3B are diagrams of the component concentration sensor, with FIG. 3A showing the state when a cell frame portion has been removed, and FIG. 3B showing the cell frame portion.
Figure 3B:
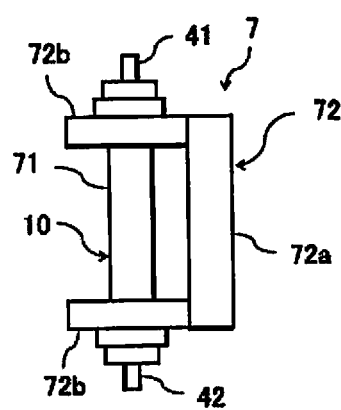

The cell unit 7 has a liquid cell portion 71 through which liquid flows, and a cell frame portion 72 that supports the liquid cell portion 71. As shown in FIG. 3B, the cell frame portion 72 has a main body portion 72a that extends linearly, and support portions 72b that extend perpendicularly from both ends of this main body portion 72a, and has a cross sectional shape resembles a square C. The support portions 72b are what support the liquid cell portion 71, and support the two ends of the liquid cell part 71 extending in one direction. That is, in the support portions 72b are able to support the liquid cell portion 71 at a position that is a specific distance away from the main body portion 72a, and in a state in which the cell unit 7 is accommodated in the housing 43, the liquid cell portion 71 is disposed between the lamp unit 8 and the effluent monitor 9, and is supported in a state in which the liquid cell portion 71 is included in the region irradiated with UV light by the lamp unit 8.

The cell unit 7 can be attached to and detached from the housing 43. More specifically, the cell frame portion 72 can be attached to and detached from the housing 43. That is, the cell frame portion 72 can be fastened with screws 73, so that when the screws 73 are removed, the cell frame portion 72 is removed as shown in FIG. 3A, and when the cell frame portion 72 is disposed between the lamp unit 8 and the effluent monitor 9 and fastened with the screws 73 as shown in FIG. 2B, it is fixed to the housing 43. More specifically, notches 44 are formed in housing 43, and in a state in which the cell frame portion 72 is in place, the end of the main body portion 72a of the cell frame portion 72 is mated with the notches 44 in a state of having a tiny gap. From this state, the cell frame portion 72 is positioned and fixed with respect to the housing 43 by tightening the screws 73 while pressing toward the notch 44 side. That is, in a state in which the cell frame portion 72 is positioned in the housing 43, as described above, the liquid cell portion 71 is held in a state of being included in the UV light irradiation area from the lamp unit 8, and is fixed such that the axial direction of the liquid cell portion 71 is parallel to the axial direction of the lamp unit 8 (a cold cathode UV lamp 81a). Consequently, even when the cell frame portion 72 has been removed, it is easy to return to the disposition state of the liquid cell portion 71 prior to detachment, merely by attaching the cell frame portion 72 to the housing 43.

Figure 4:
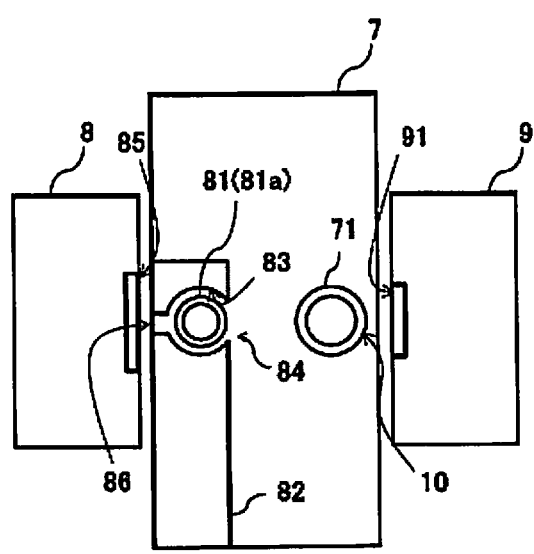
FIG. 4 is a cross section along the A-A line in FIG. 2B.

The lamp unit 8 irradiates the liquid cell portion 71 with light. The lamp unit 8 is provided at a position adjacent to the cell unit 7 in this embodiment. The lamp unit 8 is provided with an irradiation component 81, and in this embodiment, the cold cathode UV lamp 81a is provided. More specifically, as shown in FIGS. 3A and 4, the cold cathode UV lamp 81a is supported by a lamp support 82, and is fixed such that the direction in which the cold cathode UV lamp 81a extends (the axial direction) runs along the direction in which the liquid cell portion 71 extends (the axial direction). That is, the cold cathode UV lamp 81a is fixed at both ends by the lamp support 82, and is supported so that the portion to be irradiated with light will be covered by a curved portion 83. An opening 84 is formed in a portion of the lamp support 72b opposite the liquid cell portion 71, and the light of the cold cathode UV lamp 81a (irradiation component 81) is emitted from this opening 84. That is, the cold cathode UV lamp 81a emits light over the entire surface of the cylindrical tube, but the light emitted from the portion not facing the opening 84 is reflected by the curved portion 83 and emitted from the opening 84, so the light emitted from the cold cathode UV lamp 81a efficiently irradiates the liquid cell portion 71.

The effluent monitor 9 is provided at a position on the opposite side from the lamp unit 8, with the liquid cell portion 71 in between. This effluent monitor unit 9 receives light that has been emitted from the cold cathode lamp UV lamp 81a and has passed through the liquid cell portion 71. The effluent monitor unit 9 is provided with a light receiver 91, and the light receiver 91 is provided with a photodiode. This light receiver 91 is disposed on an extension of the (irradiation direction of the cold cathode UV lamp 81a, and in this embodiment is disposed at a position where the center of the cold cathode UV lamp 81a, the center of the liquid cell portion 71, and the center of the photodiode (the light receiver 91) are arranged in a straight line. The light receiving face of the light receiver 91 is formed to be opposite along the irradiation range in the lengthwise direction of the cold cathode UV lamp 81a. Consequently, light emitted from the cold cathode UV lamp 81a and transmitted through the liquid cell portion 71 can be received by the light receiver 91 without waste.

A light receiver (referred to as a second light receiver 85) is separately provided to the lamp unit 8. This second light receiver 85 monitors the light output state of the cold cathode UV lamp 81a of the lamp unit 8. More specifically, a second opening 86 is formed on the opposite side of the lamp support 72b from that of the opening 84, and the second light receiver 85 is provided opposite this second opening 86. Consequently, the light from the cold cathode UV lamp 81a (the irradiation component 81) is received directly by the second light receiver 85. In this embodiment, the second light receiver is attached on the housing 43 side, and is designed so that the electrical wiring connected to the second light receiver will not hamper operation when the cell frame portion 72 is removed. The light amount value received by this second light receiver 85 is used as a reference value for the cold cathode UV lamp 81a. That is, the light emitted from the cold cathode UV lamp 81a passes through the liquid passing through the liquid cell portion 71, and is received by the light receiver 91, so that the component concentration is sensed from the amount of light absorbed by the liquid, but if the state of the light of the cold cathode UV lamp 81a before passing through the liquid is received by the second light receiver 85, then the amount of light absorbed by the liquid can be accurately calculated on the basis of the amount of light received by the second light receiver 85. The service life of the cold cathode UV lamp 81a can also be monitored by providing a threshold value for the light amount value obtained from this second light receiver 85.

Also, in this embodiment, a cylindrical tube is used for the liquid cell portion 71 through which the liquid flows. As shown in FIG. 3B, the liquid cell portion 71 has a shape extending in one direction, and both ends thereof are supported by the support portions 72b of the cell frame portion 72. That is, the cylindrical tube is supported in a state in which the direction in which the cylindrical tube extends is the same as the direction in which the cold cathode UV lamp 81a extends, and is supported in a state in which the irradiation direction of light (the direction in which it is emitted from the irradiation component 81 toward the light receiver 91) is perpendicular to the axial direction of the cylindrical tube. That is, the cylindrical tube is supported in a state in which the outer peripheral face of the cylindrical tube is opposite the light source of the irradiation component 81.

This cylindrical tube is made of quartz. That is, if a plastic tube or the like were used for the liquid cell portion 71, the UV light of the cold cathode UV lamp 81a would be absorbed by the plastic tube, so the amount of light received by the light receiver 91 would be off by the amount of light absorbed by the plastic tube, but when quartz is used, absorption of the UV light from the cold cathode UV lamp 81a used in the irradiation component 81 by the liquid cell portion 71 is kept to a minimum, and the amount of light absorbed by the liquid flowing through the cylindrical tube can be accurately sensed.

Figure 6:
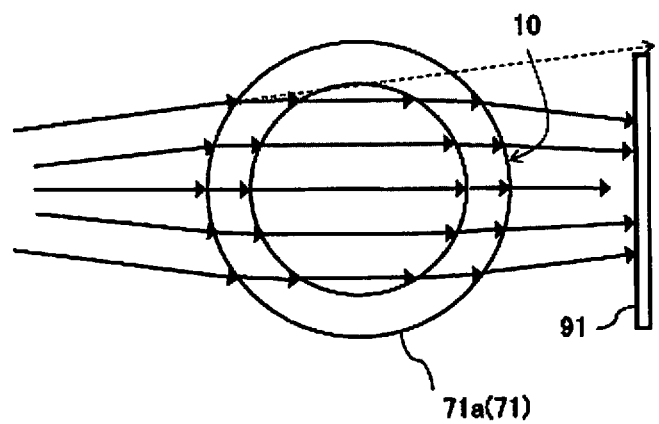
FIG. 6 is a diagram showing the path of light passing through the cylindrical tube.

Also, a light condenser 10 for condensing light that has passed through the liquid is provided between the light receiver 91 and the liquid flowing through the liquid cell portion 71. In this embodiment, the liquid cell portion 71 and the light condenser 10 are provided integrally. That is, in this embodiment, since the cylindrical tube is provided to the liquid cell portion 71, the outer peripheral face of the cylindrical tube functions as a lens (the light condenser 10), allowing the light that has passed through the liquid to be condensed and to irradiate the light receiver 91. More specifically, as shown in FIG. 6, the light emitted from the irradiation component 81 is refracted by the curved outer peripheral face 71a forming the cylindrical tube, and after passing through the liquid in the cylindrical tube of the liquid cell portion 71, the light is condensed and proceeds closer to the center of the irradiation light than it would immediately after passing through the liquid. Consequently, with the light receiver 91, the received light intensity is amplified as compared to when there is no light condensing effect, so the wavelength band absorbed by the liquid stands out clearly, and the accuracy at which the component concentration of the liquid is sensed can be improved. The broken line in FIG. 6 shows the path of the light when the light condenser 10 is not used (when using a parallel flat plate (a liquid cell portion formed in a planar shape perpendicular to the irradiation direction) instead of the cylindrical tube). In this case, since the light travels while still spread out the same way as the light emitted from the irradiation component 81, there is the risk that the light cannot be received by the light receiver 91, resulting in light quantity loss, and a decrease in the accuracy at which the component concentration in the liquid is sensed.

Figure 5:
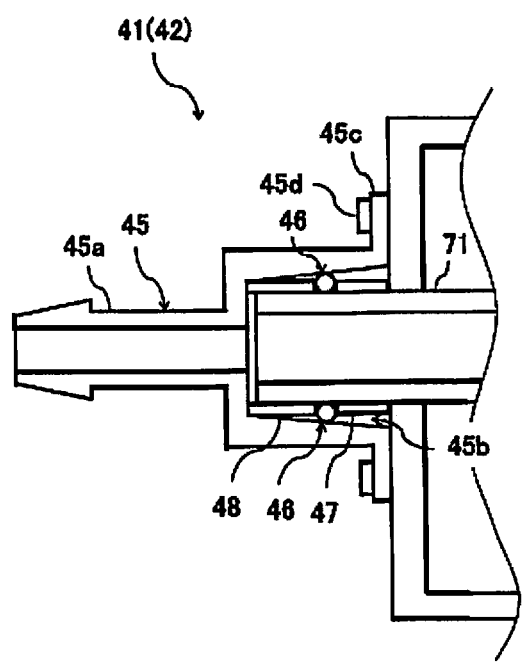
FIG. 5 is a diagram of a coupler.

Also, the liquid cell portion 71 is connected to the inlet 41 and the outlet 42. In this embodiment, the inlet 41 and the outlet 42 have the same structure. More specifically, as shown in FIG. 5, the inlet 41 is formed by a coupler 45 that covers the cylindrical tube (the liquid cell portion 71) protruding from the housing 43, and a sealing member 46 that seals the gap between the coupler 45 and the cylindrical tube. This coupler 45 has a pipe connection portion 45a that is connected to the upstream effluent line 52 (the main channel 52a in the first component concentration sensor 4a, and the branched channel 52b in the second component concentration sensor 4b), and a joint opening 45b that is connected to the liquid cell portion 71, and a flange 45c is fixed to the housing 43 by fastening it with screws 45d. The joint opening 45b is formed in a tapered shape that narrows toward the pipe connection portion 45a. Consequently, the sealing member 46 is pressed and fixed. That is, a first collar 47, a sealing member 46 (O-ring), and a second collar 48 are disposed so as to be in contact in that order, starting from the housing 43 side, with the liquid cell portion 71 (cylindrical tube) protruding from the housing 43, and in this state, the joint opening 45b is fitted and fixed. That is, when the coupler 45 is screwed to the housing 43, after the tapered portion of the joint opening 45b makes contact with the sealing member 46, the coupler 45 is further tightened with the screw 45d, so that the sealing member 46 is pressed by the tapered portion. Since the first collar 47 and the second collar 48 are adjacent on either side of the sealing member 46, the sealing member 46 pressed by the tapered portion expands and fits snugly against the cylindrical tube and the tapered portion, thereby sealing the cylindrical tube and the coupler 45. That is, the liquid that has entered the pipe connection portion 45a from the effluent line 52 flows into the cylindrical pipe without leaking from the joint opening 45b, and flows out again from the outlet portion 42 to the effluent line 52. Because the coupler 45 is configured in this way, it can be used as the liquid cell portion 71 without any machining of the cylindrical tube, and the structure will be less costly than a conventional liquid cell portion 71 having a more complicated structure.

Thus, with the first component concentration sensor 4a provided to the main channel 52a, the UV light from the irradiation component 81 that irradiates the liquid flowing in the main channel 52a passes through the cylindrical tube of the liquid cell portion 71 and is received by the light receiver 91, which allows the concentration of urea, uric acid, and the like, which are waste products in the liquid, to be measured, and allows the dialysis state of the patient during dialysis to be ascertained in real time.

Figure 7:
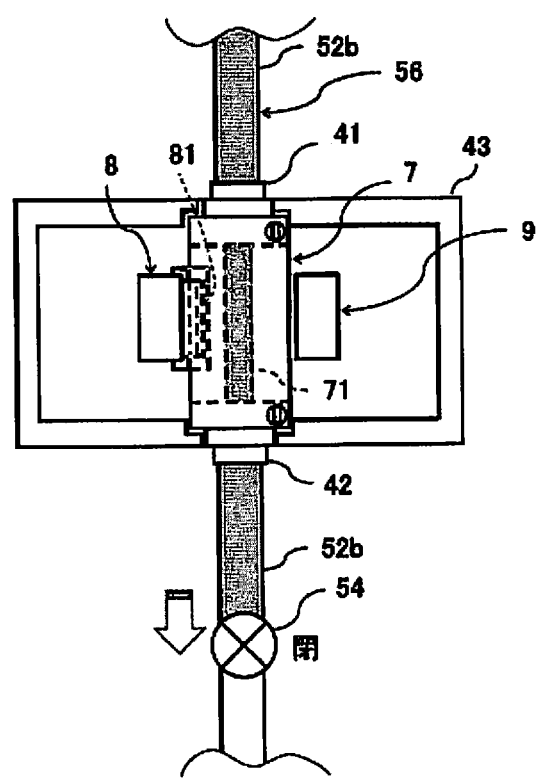
FIG. 7 is a diagram showing a state in which the collector has been formed in the branched channel with the valve closed.
Figure 8:
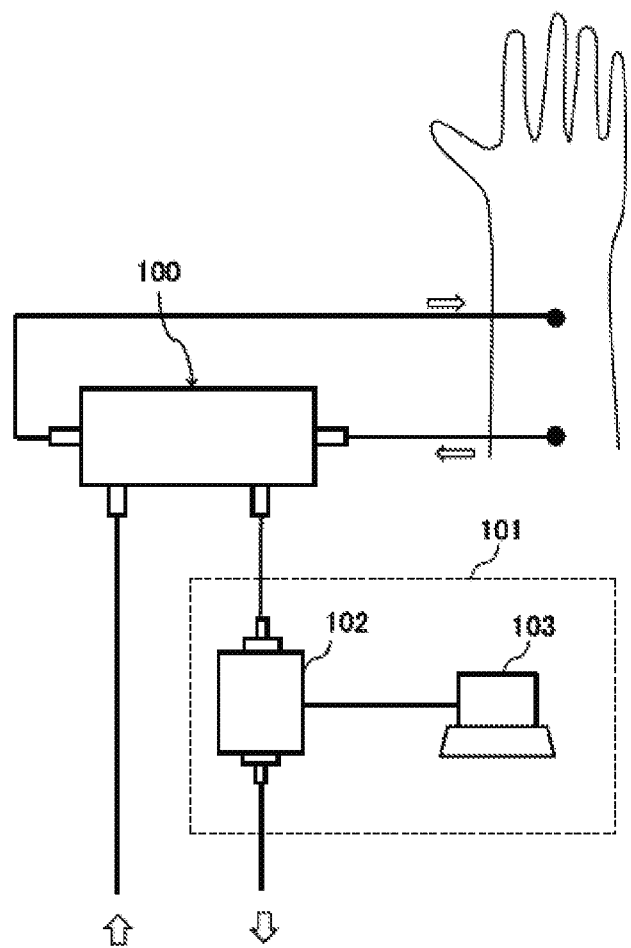
FIG. 8 is a path diagram showing a hemodialysis device to which a conventional component concentration sensing system has been applied.

Also, the second component concentration sensor 4b provided to the branched channel 52b allows the albumin concentration to be sensed. That is, in a state in which the liquid is passed through the effluent line 52 and the concentration is being measured in real time by the first component concentration sensor 4a, when the valve 54 of the branched channel 52b is closed, the liquid stops circulating. That is, as shown in FIG. 7, when the valve 54 of the branched channel 52b is closed, the liquid that was flowing through the branched channel 52b no longer has anywhere to go, and comes to a halt in the branched channel 52b (the collector 56 is formed), and as a result, the liquid flowing through the liquid cell portion 71 of the second component concentration sensor 4b connected to the branched channel 52b also collects in the liquid cell portion 71. When UV light (in this embodiment, the wavelength is set to between 240 and 260 nm) is emitted from the irradiation component 81 of the second component concentration sensor 4b, the albumin in the liquid cell portion 71 is modified over time, and the liquid in the liquid cell portion 71 becomes cloudy. That is, the light irradiating the liquid cell portion 71 is received by the light receiver 91, but the amount of light received is changed by the cloudy liquid. When the amount of albumin in the liquid changes, the cloudy state also changes, so the albumin concentration can be measured by measuring the amount of light received in this collector 56. That is, simultaneously with the observation of the progress of the dialysis state, the functional state of the liver and kidneys, the nutritional state, and the like (referred to as the health state) can also be observed. Therefore, while measuring the concentration of urea, uric acid, etc., with the first component concentration sensor 4a to ascertain the dialysis state, at the same time the albumin concentration can be detected with the second component concentration sensor 4b in the shared liquid delivery circuit, allowing the patient's health status during dialysis also to be ascertained at the same time.

In the above embodiment, the branched channel 52b was provided and the second component concentration sensor 4b was disposed on the downstream side of the first component concentration sensor 4a, but the branched channel 52b may be provided and the second component concentration sensor 4b may be disposed on the upstream side of the first component concentration sensor 4a. Again with this configuration, the albumin concentration can be measured by the second component concentration sensor 4b by collecting the liquid in the branched channel 52b.

Also, in the above embodiment, an example was given in which the UV light emitted from the irradiation component 81 was set to wavelength of 240 to 260 nm, but as long as the wavelength is one that will modify the albumin as a result of irradiation of the collected liquid, light of some other wavelength may be used instead.

In the above embodiment, an example was given in which the light condenser 10 was integrated with the liquid cell portion 71, but a member capable of condensing light into a specific region, such as a convex lens, may be disposed as the light condenser 10 between the liquid cell portion 71 and the effluent monitor 9. Here again, because the light that has passed through the liquid cell portion 71 is condensed into a specific region and received by the light receiver 91, the light reception intensity at the light receiver 91 is higher, so the accuracy at which the component concentration of the liquid is sensed can be improved.

Also, in the above embodiment, a cylindrical tube made of quartz was used for the liquid cell portion 71, but the cylindrical tube may be formed by some other member. Specifically, in the above embodiment, since UV light was emitted, quartz, which has extremely low absorption of UV light, was used as an example, but if the cylindrical tube is formed by a member that will suppress absorption of the light emitted from the irradiation component 81, the absorption of light by members other than the liquid flowing through the liquid cell portion 71 will be suppressed, which is preferable in that the concentration sensing accuracy can be enhanced.

Also, in the above embodiment, a cylindrical tube was used for the liquid cell portion 71, but if the light condenser 10 is provided separately, the liquid cell portion 71 may be formed by a parallel plate that is perpendicular to the light from the irradiation component 81 (a liquid cell portion formed in a planar shape perpendicular to the irradiation direction).

Also, in the above embodiment, an example was given in which the cold cathode UV lamp 81a was used in the irradiation component 81 to keep the cost low, but an LED lamp may be used instead.

Also, in the above embodiment, an example was given in which the liquid cell portion 71 was provided to the cell frame portion 72, and the cell frame portion 72 was detachable, but the liquid cell portion 71 may be integrated with the housing 43 and fixed directly.

The invention claimed is:

1. A component concentration sensing system comprising:
   a first component concentration sensor that is provided to a channel through which flows a liquid whose component concentration is to be sensed, and that is configured to irradiate the liquid with light and sense the component concentration in the liquid from a degree of light absorption;
   a collector that is arranged to collect the liquid flowing through the channel; and
   a second component concentration sensor that is configured to irradiate the liquid collected in the collector with light and sense the component concentration in the liquid from the degree of light absorption.

2. The component concentration sensing system according to claim 1, wherein
   the collector includes a branched channel that branches off from the channel to which the liquid is fed, and a valve that is provided to the branched channel, and
   the second component concentration sensor is configured to sense the component concentration of the liquid collected in the branched channel.

3. The component concentration sensing system according to claim 2, wherein
   the first and second component concentration sensors have an irradiation component that is configured to emit light, a light receiver that is configured to receive the light emitted from the irradiation component, and a liquid cell portion that is disposed between the irradiation component and the light receiver and through which the liquid flows, and
   the liquid cell portion is formed of a cylindrical tube.

4. The component concentration sensing system according to claim 3, wherein
   the liquid is an effluent discharged from a blood purification device, and
   the light that irradiates the effluent has a wavelength of 240 to 260 nm.

5. The component concentration sensing system according to claim 2, wherein
   the liquid is an effluent discharged from a blood purification device, and
   the light that irradiates the effluent has a wavelength of 240 to 260 nm.

6. The component concentration sensing system according to claim 1, wherein
   the first and second component concentration sensors have an irradiation component that is configured to emit light, a light receiver that is configured to receive the light emitted from the irradiation component, and a liquid cell portion that is disposed between the irradiation component and the light receiver and through which the liquid flows, and the liquid cell portion is formed of a cylindrical tube.

7. The component concentration sensing system according to claim 6, wherein the liquid is an effluent discharged from a blood purification device, and the light that irradiates the effluent has a wavelength of 240 to 260 nm.

8. The component concentration sensing system according to claim 1, wherein the liquid is an effluent discharged from a blood purification device, and the light that irradiates the effluent has a wavelength of 240 to 260 nm.

* * * * *